United States Patent
de Groot

(10) Patent No.: US 10,687,495 B2
(45) Date of Patent: Jun. 23, 2020

(54) WATERMELON VARIETY NUN 11603 WMW

(71) Applicant: NUNHEMS B.V., Nunhem (NL)

(72) Inventor: Erik de Groot, Nonantola (IT)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/229,651

(22) Filed: Dec. 21, 2018

(65) Prior Publication Data

US 2019/0116751 A1 Apr. 25, 2019

Related U.S. Application Data

(60) Provisional application No. 62/688,876, filed on Jun. 22, 2018.

(51) Int. Cl.
*A01H 6/34* (2018.01)
*A01H 5/08* (2018.01)

(52) U.S. Cl.
CPC .............. *A01H 6/342* (2018.05); *A01H 5/08* (2013.01)

(58) Field of Classification Search
CPC .................................. A01H 5/08; A01H 6/342
See application file for complete search history.

(56) References Cited

U.S. PATENT DOCUMENTS

| | | | |
|---|---|---|---|
| 9,402,357 B1 * | 8/2016 | Brusca | A01H 5/10 |
| 2006/0168701 A1 | 7/2006 | Zhang et al. | |
| 2015/0126380 A1 | 5/2015 | Van Dun | |
| 2015/0245570 A1 | 9/2015 | Vogelaar et al. | |

FOREIGN PATENT DOCUMENTS

WO 2010111031 A1 9/2010

OTHER PUBLICATIONS

"Objective description of Variety—Watermelon (*Citrillus lanatus* Thunb.) Matsum. & Nakai", U.S. Department of Agriculture Agricultural Marketing Service Science and Technology Plant Variety Protection Office, Exhibit C, 2015, 4 pages.
Compton et al., "Use of Tissue Culture and Biotechnology for the Genetic Improvement of Watermelon," Plant Cell, Tissue and Organ Culture, 2004, vol. 77, pp. 231-243.
Hayata et al., "Synthetic Cytokinin-1-(2=chloro=4=pyridyl)-3-phenylurea (CPPU)—Promotes Fruit Set and Induces Parthenocarpy in Watermelon" Society of Horticultural Science, vol. 120, Issue 6, 1995, pp. 997-1000.
Hitoshi Kihara, "Triploid Watermelon" Proceedings of American Society for Horticultural Science, vol. 58, 1951, pp. 217-230.
Moussa et al., "Parthenocarpy of Watermelon Cultivars Induced by γ-Irradiation" Russian Journal of Plant Physiology, vol. 57, Issue 4, 2010, pp. 574-581.
Needleman et al., "A General Method Applicable to the Search for Similarities in the Amino Acid Sequence of Two Proteins," Journal of Molecular Biology, vol. 48, Issue 3, 1970, pp. 443-453.
Nikolova et al., "Diploidization of Cucumber (*Cucumis sativus* L.) Haploids by Colchini Treatment", Acta Societas Botanicorum Poloniae, vol. 65, 1996, pp. 311-317.
O. Eigsti, "About our cover" HortScience, vol. 6, 1971, 1 page.
Parvathaneni et al., "Fingerprinting in Cucumber and Melon (*Cucumis* spp.) Genotypes Using Morphological and ISSR Markers", Journal of Crop Science and Biotechnology, vol. 14, Issue 1, Mar. 2011, pp. 39-43.
Rice et al., "Emboss: The European Molecular Biology Open Software Suite" Trends in Genetics, vol. 16, Issue 6, 2000, pp. 276-277.
Upov, "Guidelines for the Conduct of Tests for Distinctness, Uniformity and Stability", TG 142/5, International Union for the Protection of New Varieties of Plants, Geneva Mar. 20, 2013, 39 pages.
Viddavsky et al., "Tomato Breeding Lines Resistant and Tolerant to Tomato Yellow Leaf Curl Virus Issued from Lycopersicon hirsutum", The American Phytopathology Society, vol. 88, Issue 9, 1998, pp. 910-914.
Vos et al., "AFLP: a new technique for DNA fingerprinting", Nucleic Acid Research, vol. 23, Issue 21, 1995, pp. 4407-4414.
Wijnker et al., "Hybrid recreation by reverse breeding in *Arabidopsis thaliana*", Nature Protocols, vol. 9, 2014, pp. 761-772.

\* cited by examiner

*Primary Examiner* — Lee A Visone
(74) *Attorney, Agent, or Firm* — Arent Fox LLP

(57) ABSTRACT

The invention provides a new and distinct hybrid variety of watermelon, NUN 11603 WMW as well as seeds and plants and fruits thereof.

20 Claims, No Drawings

WATERMELON VARIETY NUN 11603 WMW

CROSS-REFERENCE TO RELATED APPLICATION

This application claims priority to U.S. Provisional Application No. 62/688,876, filed Jun. 22, 2018, which is hereby incorporated by reference in its entirety.

FIELD OF THE DISCLOSURE

The disclosure relates to the field of plant breeding and, more specifically, to watermelon variety NUN 11603 WMW. The disclosure further relates to vegetative reproductions of NUN 11603 WMW, methods for tissue culture of NUN 11603 WMW and regenerating a plant from such a tissue culture and to phenotypic variants of NUN 11603 WMW.

BACKGROUND

The goal of plant breeding is to combine various desirable traits in a single variety or hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One valuable crop that has been subject to breeding programs is watermelon, a member of the Cucurbitacea family. The genus Citrullus originated in Africa. The plant is a large and sprawling annual, grown for its fruit. Watermelon fruit is often colored attractively, commonly red. Watermelon can contain black seeds, which are considered undesirable for certain uses.

Watermelon (Citrullus lanatus) can occur as a diploid, triploid or tetraploid. Seedless watermelon fruits are produced by using pollen from diploid male parent plants to fertilize flowers of tetraploid maternal parent plants. Pollination of the tetraploid flowers with diploid pollen leads to hybrid F1 seeds which are triploid (see, e.g., Kihara, 1951, Proceedings of American Society for Horticultural Science 58: 217-230; Eigsti 1971, Hort Science 6: 1-2). The triploid hybrid plants grown from these F1 seeds are self-infertile as they produce sterile pollen due to chromosome imbalance and need to be pollinated by a diploid pollenizer to produce watermelon fruit. Triploid plants are, therefore, interplanted with pollenizer plants for fruit production. The "seedless" fruit produced after pollination on the triploid hybrid plant are not truly seedless, but often contain some undeveloped, small, pale seeds, which are edible. Plants are generally planted at a ratio of 1 pollenizer per every 2-4 triploid plants. Triploid plants and pollenizers are either planted in separate rows (e.g., 1 row of pollenizer and 2-4 rows of triploids), or interplanted within rows (e.g., planting 1 pollenizer plant in between 2 to 3 triploid plants in the same row), or interplanted in narrow rows between rows of triploids (see e.g., Table 2 of US2006/0168701 and WO2010/111031), which is herein incorporated by reference in its entirety). The fruit produced on the pollenizer plants preferably has a different rind pattern from the fruit on the triploid hybrids, so that these can be easily distinguished.

Grading of fruits is usually done by fruit weight, to distinguish "mini" watermelons, with weights of less than 6 pounds (2.72 kg), "icebox" watermelons with weights of 8-12 pounds (3.62 kg-5.44 kg) or, according to others, of 6 to 15 pounds (2.72 kg to 6.8 kg) and "picnic" watermelons of above the icebox size, so either above 12 lb (above 5.44 kg) or above 15 pounds (above 6.8 kg). Furthermore, watermelon fruit flesh can have various colors, including various tints of red, pink, orange and yellow.

Many different watermelon cultivars have been produced, and watermelon breeding efforts have been underway in many parts of the world. Breeding objectives include varying the color, shape, texture and flavor of the fruit, absence of seeds, disease or pest resistance, optimizing flesh thickness, yield, suitability to various climatic circumstances, solid content (% dry matter), and sugar content.

Although hybrid triploid (seedless) watermelons have been grown in the United States for many decades, there is still a need for improved varieties. Consumer demand is high, and the seedless fruit of triploid watermelons are highly desired, both for the fresh and the processed markets. Many different triploid watermelon varieties exist (see, e.g., http://cucurbitbreeding.com/todd-wehner/publications/watermelon-breeding), producing fruits of different sizes and shapes, as well as different fruit quality.

SUMMARY OF VARIOUS EMBODIMENTS OF THE DISCLOSURE

The disclosure provides for watermelon variety NUN 11603 WMW, products thereof, and methods of using the same. NUN 11603 WMW is a mini watermelon and is suitable for growing in tunnel high or open field environment.

In one aspect, the disclosure provides a seed of NUN 11603 WMW, wherein a representative sample of said seed has been deposited under Accession Number NCIMB 43061. The disclosure also provides for a plurality of seeds of NUN 11603 WMW. The watermelon seed of NUN 11603 WMW may be provided as an essentially homogeneous population of watermelon seed. The population of seed of NUN 11603 WMW may be particularly defined as essentially free from other seed. The seed population may be grown into plants to provide an essentially homogeneous population of watermelon plants as described herein.

The disclosure also provides a plant grown from a seed of watermelon variety NUN 11603 WMW and a plant part thereof. In another aspect, the disclosure provides for a hybrid watermelon variety NUN 11603 WMW. The disclosure also provides for a progeny of NUN 11603 WMW. In another aspect, the disclosure provides a plant or a progeny retaining all or all but one, two or three of the "distinguishing characteristics" or all or all but one, two or three of the "morphological and physiological characteristics" of NUN 11603 WMW and methods for producing that plant or progeny.

In one aspect, the disclosure provides a plant or a progeny having all the physiological and morphological characteristics of NUN 11603 WMW when grown under the same environmental conditions. In another aspect, the plant or progeny has all or all but one, two or three of the physiological and morphological characteristics of NUN 11603 WMW when measured under the same environmental conditions and e.g., evaluated at significance levels of 1%, 5% or 10% significance (which can also be expressed as a p-value) for quantitative characteristics, wherein a representative sample of seed of NUN 11603 WMW has been deposited under Accession Number NCIMB 43061. In another aspect, the plant or progeny has all or all but one, two or three of the physiological and morphological characteristics as listed in Table 1 and/or 2 for NUN 11603 WMW when measured under the same environmental conditions and e.g., evaluated at significance levels of 1%, 5% or 10% significance (which can also be expressed as a p-value) for quantitative characteristics.

In another aspect, a plant of NUN 11603 WMW or a progeny thereof has 8, 9, or more or all of the following distinguishing characteristics as shown in Table 1 and/or 2:1) average length of petiole; 2) average length of leaf; 3) average number of stems at crown; 4) average weigh of mature fruit; 5) average length of mature fruit; 6) average diameter at midsection of mature fruit; 7) average thickness of stem end; 8) average firmness of fruit; 9) ploidy; and/or 10) secondary color of mature fruit.

In other aspects, the disclosure provides for a plant part obtained from NUN 11603 WMW, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a scion, a stock, a rootstock, a pistil, an anther, or a flower or a part thereof. Fruits are particularly important plant parts. In another aspect, the plant part obtained from NUN 11603 WMW is a cell, optionally a cell in a cell or tissue culture. That cell may be grown into a plant of NUN 11603 WMW.

The disclosure also provides a cell culture of NUN 11603 WMW and a plant regenerated from NUN 11603 WMW, which plant has all the characteristics of NUN 11603 WMW when grown under the same environmental conditions, as well as methods for culturing and regenerating NUN 11603 WMW. Alternatively, a regenerated plant may have one characteristic that is different from NUN 11603 WMW.

The disclosure further provides a vegetatively propagated plant of NUN 11603 WMW having all or all but one, two or three of the morphological and physiological characteristics of NUN 11603 WMW when grown under the same environmental conditions.

The disclosure furthermore provides a watermelon fruit produced on a plant grown from a seed of NUN 11603 WMW.

In another aspect the disclosure provides a seed growing or grown on a plant of NUN 11603 WMW (i.e., produced after pollination of the flower of NUN 11603 WMW).

Definitions

"Watermelon" refers herein to plants of the species *Citrullus lanatus*. The most commonly eaten part of a watermelon is the fruit. The fruit comprises a stem and peduncle or pedicel, receptacle, ectocarp, rind, fruit flesh, exocarp, mesocarp, external phloem, internal phloem, xylem, vascular bundle, carpel, placenta and optionally seed. The stem and peduncle or pedicel, receptacle, ectocarp, rind, fruit flesh, exocarp, mesocarp, external phloem, internal phloem, xylem, vascular bundle, carpel, placenta and seedcoat of the seed are maternal tissues, and genetically identical to the plant on which they grow.

"Cultivated watermelon" refers to plants of *Citrullus lanatus* (e.g., varieties, breeding lines or cultivars of the species *C. lanatus*), cultivated by humans and having good agronomic characteristics.

The terms "watermelon plant designated NUN 11603 WMW", "NUN 11603 WMW", "NUN 11603", "NUN 11603 F1", "11603 WMW" or "watermelon 11603" are used interchangeably herein and refer to a NUN 11603 WMW plant of, representative seed of which having been deposited under Accession Number NCIMB 43061.

A "seed of NUN 11603 WMW" refers to a watermelon seed which can be grown into a plant of NUN 11603 WMW, wherein a representative sample of viable seed of NUN 11603 WMW has been deposited under Accession Number NCIMB 43061. A seed can be in any stage of maturity, for example, a mature, viable seed, or an immature, non-viable seed. A seed comprises an embryo and maternal tissues.

An "embryo of NUN 11603 WMW" refers to an "F1 hybrid embryo" as present in a seed of NUN 11603 WMW, a representative sample of said seed of NUN 11603 WMW having been deposited under Accession Number NCIMB 43061.

A "seed grown on NUN 11603 WMW" refers to a seed grown on a mature plant of NUN 11603 WMW or inside a fruit of NUN 11603 WMW. The "seed grown on NUN 11603 WMW" contains tissues and DNA of the maternal parent, NUN 11603 WMW. The "seed grown on NUN 11603 WMW" contains an F2 embryo. When said seed is planted, it grows into a first generation progeny plant of NUN 11603 WMW.

A "fruit of NUN 11603 WMW" refers to a fruit containing maternal tissues of NUN 11603 WMW as deposited under Accession Number NCIMB 43061. In one option, the fruit contains seed grown on NUN 11603 WMW. In another option, the fruit does not contain seed, that is the fruit is parthenocarpic. The skilled person is familiar with methods for inducing parthenocarpy. Those methods comprise chemically or genetically inducing parthenocarpy, or by use of irradiated pollen (see, e.g., Moussa and Salem, 2010). Compounds suitable for chemically inducing parthenocarpy include auxins, gibberellins and cytokinins (see, e.g., Hayata et al., 1995). A fruit can be in any stage of maturity, for example, a mature fruit in the stage comprising viable seed, or an immature fruit comprising non-viable seed.

An "essentially homogeneous population of watermelon seed" is a population of seeds where at least 97%, 98%, 99% or more of the total population of seed are seed of NUN 11603 WMW.

An "essentially homogeneous population of watermelon plants" is a population of plants where at least 97%, 98%, 99% or more of the total population of plants are plants of NUN 11603 WMW.

The phrase "essentially free from other seed" refers to a population of seed where less than 3%, 2%, 1% or less of the total population of seed is seed that is not a watermelon seed or, in another aspect, less than 3%, 2%, 1% or less of the total population of seed is seed that is not seed of NUN 11603 WMW.

"Tissue culture" or "cell culture" refers to a composition comprising isolated cells of the same or a different type or a collection of such cells organized into parts of a plant. Tissue culture of various tissues of watermelon and regeneration of plants therefrom is well known and widely published (see, e.g., Compton et al., Plant Cell, Tissue and Organ Culture 77: 231-243, 2004). Similarly, methods for preparing a "tissue culture" or "cell culture" are well known in the art.

"USDA descriptors" are the plant variety descriptors for Watermelon in the "Objective Description of Variety—Watermelon (*Citrullus lanatus*)", as published by the US Department of Agriculture, Agricultural Marketing Service, Plant Variety Protection Office, Beltsville, Md. 20705 and which can be downloaded from the world-wide web at ams.usda.gov/sites/under services/plant-variety-protection/pvpo-c-forms under watermelon. "Non-USDA descriptors" are other descriptors suitable for describing watermelon.

"UPOV descriptors" are the plant variety descriptors described for watermelon in the "Guidelines for the Conduct of Tests for Distinctness, Uniformity and Stability, TG/142/5 (Geneva, 2013), as published by UPOV (International Union for the Protection of New Varieties and Plants) and which can be downloaded from the world-wide web at upov.int/edocs/tgdocs/en/tg142.pdf and is herein incorporated by reference in its entirety. Likewise, "UPOV methods" to determine the specific parameters for the characterization of melon are described at upov.int.

"RHS" or "RHS color chart" refers to the color chart of the Royal Horticultural Society (UK), which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS colour chart 2007.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of NUN 11603 WMW and an embryo having one or two sets of chromosomes derived from the parent plant, e.g., from NUN 11603 WMW. Such an embryo comprises two sets of chromosomes derived from NUN 11603 WMW, if it is produced from self-pollination of NUN 11603 WMW, while an embryo derived from cross-fertilization of NUN 11603 WMW will comprise only one set of chromosomes from said variety.

"Reference Variety" for NUN 11603 WMW refers herein to Premium which has been planted in a trial together with NUN 11603 WMW. USDA descriptors of NUN 11603 WMW were compared to the USDA descriptors of Premium.

"Rootstock" or "stock" refers to the plant selected for its root system, in particular for the resistance of the roots to diseases or stress (e.g., heat, cold, salinity etc.). Generally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired watermelon fruit.

"Stock/scion" or "grafted plant" refers to a watermelon plant comprising a rootstock from one plant grafted to a scion from another plant.

"Harvest maturity" is referred to as the stage at which a watermelon fruit is ripe or ready for harvest or the optimal time to harvest the fruit for the market, for processing or for consumption. In one aspect, harvest maturity is the stage which allows proper completion of the normal ripening.

"Flavor" refers to the sensory impression of a food or other substance, especially a watermelon fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of watermelon fruits or fruit parts (fruit flesh).

"Harvested plant material" refers herein to plant parts (e.g., fruits detached from the whole plant), which have been collected for further storage and/or further use.

"Yield" means the total weight of all watermelon fruits harvested per hectare of a particular line or variety. It is understood that "yield" expressed as weight of all watermelon fruits harvested per hectare can be obtained by multiplying the number of plants per hectare times the "yield per plant".

"Marketable yield" means the total weight of all marketable watermelon fruits, especially fruit which is not cracked, damaged or diseased, harvested per hectare of a particular line or variety. A "marketable fruit" is a fruit that has commercial value.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical (quantitative), or for having an identical degree (or type) if not numerical (not quantitative), if measured under the same environmental conditions. For example, a progeny plant or a Single Locus Converted plant or a mutated plant of NUN 11603 WMW may have one or more (or all) of the essential physiological and/or morphological characteristics of said variety listed in Table 1 and/or 2, as determined at the 5% significance level (i.e., p<0.05), when grown under the same environmental conditions.

"Distinguishing characteristics" or "distinguishing morphological and/or physiological characteristics" refers herein to the characteristics which distinguish the new variety from other watermelon varieties, such as the Reference Variety (e.g., are different), when grown under the same environmental conditions. The distinguishing characteristics between NUN 11603 WMW and Reference Variety are described herein and also can be seen in Table 1 and/or 2. When comparing NUN 11603 WMW to other varieties, the distinguishing characteristics may be different. In one aspect, the distinguishing characteristics may include one, two, three or more (or all) of the characteristics listed in Table 1 and/or 2. All numerical distinguishing characteristics are statistically significantly different at p<0.05 between NUN 11603 WMW and the other variety (e.g., the Reference Variety).

NUN 11603 WMW has the following distinguishing characteristics when compared to the Reference Variety as shown in Table 1 and/or 2:1) average length of petiole; 2) average length of leaf; 3) average number of stems at crown; 4) average weigh of mature fruit; 5) average length of mature fruit; 6) average diameter at midsection of mature fruit; 7) average thickness of stem end; 8) average firmness of fruit; 9) ploidy; and 10) secondary color of mature fruit. This can be seen in Table 1 and/or 2, where the characteristics of NUN 11603 WMW are compared to the characteristics of the Reference Variety, when grown under the same environmental conditions Thus, a watermelon plant "comprising the distinguishing characteristics of NUN 11603 WMW" (such as a progeny plant) refers herein to a plant which does not differ significantly from said variety in the distinguishing characteristics above. Therefore, in one aspect, a plant is provided which does not differ significantly from NUN 11603 WMW in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using one way analysis of variance (ANOVA), a standard method known to the skilled person. Non-numerical or "degree" or "type" characteristic is considered "the same" when the values have the same "degree" or "type" when scored using USDA and/or UPOV descriptors, if the plants are grown under the same environmental conditions.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a plant part and inducing or allowing that plant part to form at least roots, and also refer to the plant or plantlet obtained by that method.

Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

A "pollenizer" is a watermelon plant that can be used to pollenize triploids. Preferably, such a plant produces a very large amount of pollen.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one watermelon line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 11603 WMW. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another watermelon plant of the same variety or another variety or line, or with wild watermelon plants. A progeny may comprise a mutation or a transgene. A "first generation progeny" is the progeny directly derived from, obtained from, or derivable from the parent plant by, e.g., traditional breeding methods (selfing and/or cross-pollinating) or regeneration (optionally combined with transformation or mutation). Thus, a plant of NUN 11603 WMW is the male parent, the female parent or both of a first generation progeny of NUN 11603 WMW. Progeny may have all the physiological and morphological characteristics of NUN 11603 WMW, when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of NUN 11603 WMW.

The terms "gene converted" or "conversion plant" or "single locus converted plant" in this context refer to watermelon plants which are developed by traditional breeding techniques, e.g., backcrossing or via genetic engineering or through mutation breeding, wherein essentially all of the desired morphological and physiological characteristics of the parent variety or line are recovered, in addition to the one or more characteristics introduced into the parent via e.g., the backcrossing technique (optionally including reverse breeding or reverse synthesis of breeding lines). It is understood that not only the addition of a further characteristic (e.g., addition of gene conferring a further characteristic, such as a disease resistance gene), but also the replacement/modification of an existing characteristic by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of a watermelon variety are recovered in addition to the characteristics of the single locus having been transferred into the variety via the abovementioned technique, or wherein the morphological and physiological characteristics of the variety has been replaced/modified in the variety. In case of a hybrid, the gene may be introduced in the male or female parental line.

"Average" refers herein to the arithmetic mean.

The term "mean" refers to the arithmetic mean of several measurements. The skilled person understands that the appearance of a plant depends to some extent on the growing conditions of said plant. Thus, the skilled person will know suitable growing conditions for NUN 11603 WMW. The mean, if not indicated otherwise within this application, refers to the arithmetic mean of measurements on at least 10 different, randomly selected plants of a variety or line.

DETAILED DESCRIPTION OF VARIOUS EMBODIMENTS OF THE DISCLOSURE

The disclosure relates to a plant of NUN 11603 WMW, wherein a representative sample of seeds of said variety has been deposited under the Budapest Treaty, with Accession number NCIMB 43061. NUN 11603 WMW is a mini watermelon variety and is suitable for growing in tunnel high and open field environment.

The disclosure also relates to a seed of a new watermelon variety NUN 11603 WMW, wherein a representative sample of said seed has been deposited under the Budapest Treaty, with Accession number NCIMB 43061.

In another aspect, the disclosure provides for a watermelon plant part of NUN 11603 WMW, such as a fruit, a representative sample of seed from said variety has been deposited under the Budapest Treaty, with Accession number NCIMB 43061.

A seed of hybrid variety NUN 11603 WMW is obtainable by crossing the male parent of NUN 11603 WMW with the female parent of NUN 11603 WMW and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 11603 WMW.

Also provided is a plant of NUN 11603 WMW, or a fruit or other plant part thereof, produced from a seed, wherein a representative sample of said seeds has been deposited under the Budapest Treaty, with Accession Number NCIMB 43061.

Also provided is a plant part obtained from NUN 11603 WMW, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety hypocotyl, cotyledon, a scion, a stock, a rootstock, a pistil, an anther, and a flower or a part thereof. Fruits are particularly important plant parts. Fruits may be parthenocarpic, or seedless, or contain immature or nonviable seeds, or contain viable seeds.

In a further aspect, the plant part obtained from variety NUN 11603 WMW is a cell, optionally a cell in a cell or tissue culture. That cell may be grown into a plant of NUN 11603 WMW. A part of NUN 11603 WMW (or of a progeny of that variety or of a plant having all physiological and/or morphological characteristics but one, two or three of NUN 11603 WMW) further encompasses any cells, tissues, organs obtainable from the seedlings or plants in any stage of maturity.

The disclosure also provides for a food or feed product or a processed product comprising or consisting of a plant part described herein. Preferably, the plant part is a watermelon fruit or part thereof and/or an extract from a fruit or another plant part described herein comprising at least one cell of NUN 11603 WMW. The food or feed product may be fresh or processed, e.g., dried, grinded, powdered, pickled, chopped, cooked, roasted, in a sauce, in a sandwich, pasted, pureed or concentrated, juiced, pickled, canned, steamed, boiled, fried, blanched and/or frozen, etc.

Such a plant part of NUN 11603 WMW can be stored and/or processed further. The disclosure thus also provides for a food or feed product comprising one or more of such parts, such as canned, chopped, cooked, roasted, in a sauce, in a sandwich, pasted, pureed or concentrated, juiced, frozen, dried, pickled, or powdered watermelon fruit from NUN 11603 WMW or from progeny of said variety, or from a derived variety, such as a plant having all but one, two or three physiological and/or morphological characteristics of NUN 11603 WMW.

In another aspect, the disclosure provides for a watermelon fruit of NUN 11603 WMW, or a part of a fruit of said variety. The fruit can be in any stage of maturity, for example, immature or mature. In another embodiment, the disclosure provides for a container comprising or consisting of a plurality of harvested watermelon fruits or parts of fruits of said variety, or fruits of progeny thereof, or fruits of a derived variety.

Marketable fruits are generally sorted by size and quality after harvest. Alternatively, the fruits can be sorted by expected shelf life, pH or Brix.

In another aspect, the plant, plant part or seed of NUN 11603 WMW is inside one or more containers. For example, the disclosure provides contains such as cans, boxes, crates, bags, cartons, Modified Atmosphere Packaging, films (e.g. biodegradable films), etc. comprising a plant or a plant part (fresh and/or processed) or a seed of NUN 11603 WMW. In a particular aspect, the container comprises a plurality of seeds of NUN 11603 WMW, or a plurality of plant parts of NUN 11603 WMW.

The disclosure further relates to a watermelon variety, referred to as NUN 11603 WMW, which when compared to its Reference Variety NUN 4001 WM has the following distinguishing characteristics as shown in Table 1 and/or 2: 1) average length of petiole; 2) average length of leaf; 3) average number of stems at crown; 4) average weigh of mature fruit; 5) average length of mature fruit; 6) average diameter at midsection of mature fruit; 7) average thickness of stem end; 8) average firmness of fruit; 9) ploidy; and 10) secondary color of mature fruit, where the characteristics are determined at the 5% significance level for plants grown under the same environmental conditions. Also encompassed are parts of that plant.

In one aspect, a plant of NUN 11603 WMW or a progeny plant thereof, comprises all of the following morphological and/or physiological characteristics (i.e., average values of distinguishing characteristics, as indicated on the USDA Objective description of variety—watermelon (unless indicated otherwise)) as shown in Table 1 and/or 2:1) average length of petiole; 2) average length of leaf, 3) average number of stems at crown; 4) average weigh of mature fruit; 5) average length of mature fruit; 6) average diameter at midsection of mature fruit; 7) average thickness of stem end; 8) average firmness of fruit; 9) ploidy; and 10) secondary color of mature fruit, where the characteristics are determined at the 5% significance level for plants grown under the same environmental conditions. An example of values for the distinguishing characteristics collected in a trial run can be found in Table 1 and/or 2. A part of this plant is also provided.

NUN 11603 WMW may further exhibit one or more of the following traits: a) average size of leaf, and b) shape of mature fruit.

In another aspect, NUN 11603 WMW comprises resistance to *Fusarium oxysporum* f. sp. *niveum* Race 1 and/or to *Colletotrichum orbiculare* Race 1, measured according to UPOV standards described in TG/142/5.

The disclosure further provides a watermelon plant which does not differ from the physiological and morphological characteristics of the plant of NUN 11603 WMW as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a fruit or part thereof.

The disclosure also provides a tissue or cell culture comprising cells of NUN 11603 WMW. Such a tissue culture can, for example, be grown on plates or in liquid culture, or be frozen for long term storage. The cells of NUN 11603 WMW used to start the culture can be selected from any plant part suitable for vegetative reproduction, or in a particular aspect can be cells of an embryo, meristem, a cotyledon, a hypocotyl, pollen, a leaf, an anther, a root, a root tip, a pistil, a petiole, a flower, a fruit, seed or a stem.

In another particular aspect, the tissue culture does not contain somaclonal variation or has reduced somaclonal variation. The skilled person is familiar with methods to reduce or prevent somaclonal variation, including regular re-initiation.

In one aspect, the disclosure provides a watermelon plant regenerated from the tissue or cell culture of NUN 11603 WMW, wherein the regenerated plant is not significantly different from NUN 11603 WMW in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a watermelon plant regenerated from the tissue or cell culture of NUN 11603 WMW, wherein the plant has all of the physiological and morphological characteristics of said variety determined at the 5% significance level when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

NUN 11603 WMW, or its progeny, or a plant having all physiological and/or morphological characteristics but one, two or three which are different from those of NUN 11603 WMW, can also be reproduced using vegetative reproduction methods. Therefore, the disclosure provides for a method of producing a plant, or a plant part, of NUN 11603 WMW, comprising vegetative propagation of said variety. Vegetative propagation comprises regenerating a whole plant from a plant part of NUN 11603 WMW or from a progeny or from or a plant having all physiological and/or morphological characteristics of said variety but one, two or three different characteristics, such as a cutting, a cell culture or a tissue culture.

The disclosure also provides methods of vegetatively propagating a part of the plant of the disclosure NUN 11603 WMW. In certain aspects, the method comprises: (a) cultivating tissue or cells capable of being propagated from NUN 11603 WMW to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one embodiment, the method further comprises step (c) growing plants from said rooted plantlets. Therefore, the method also comprises regenerating a whole plant from a part of NUN 11603 WMW. In a particular aspect, the part of the plant to be propagated is is a cutting, a cell culture or a tissue culture.

The disclosure also provides for a vegetatively propagated plant of NUN 11603 WMW (or from progeny of NUN 11603 WMW or from or a plant having all but one, two or three physiological and/or morphological characteristics of NUN 11603 WMW), wherein the plant has all of the morphological and physiological characteristics of NUN 11603 WMW when the characteristics are determined at the 5% significance level for plants grown under the same conditions. In another aspect, the propagated plant has all but one, two or three of the morphological and physiological characteristics of NUN 11603 WMW when the characteristics are determined at the 5% significance level for plants grown under the same conditions. A part of said propagated plant or said propagated plant with one, two or three differences is also provided.

In another aspect, the disclosure provides a method for producing a watermelon plant part, preferably a fruit, comprising growing a plant of NUN 11603 WMW until it sets at least one fruit, and collecting the fruit. Preferably, the fruit is collected at harvest maturity. In another aspect, the fruit is collected when the seed is ripe. In a particular aspect, all fruits on a truss can be harvested together. In another particular aspect, all fruit on a watermelon plant can be harvested at the same time. A plant of NUN 11603 WMW can be produced by seeding directly in the soil (e.g., the field) or by germinating the seeds in a controlled environment (e.g., greenhouse) and optionally then transplanting the seedlings into the field (see, e.g., https://anrcatalog.ucanr.edu/pdf/7213.pdf). Watermelon can also be grown entirely in greenhouses. For example, a seed is sown into a prepared seed bed in a field where the plant remains for its entire life. Alternatively, the seed may be planted through a black plastic mulch. The dark plastic will absorb heat from the sun, warming the soil early. It will also help to conserve moisture during the growing season, controls weed and makes harvesting easier and cleaner. Triploid varieties should be interplanted with pollenizers to set fruit.

In still another aspect, the disclosure provides a method of producing a watermelon plant, comprising crossing a plant of NUN 11603 WMW with a second watermelon plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent watermelon plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for developing a watermelon plant in a watermelon breeding program, using NUN 11603 WMW, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 11603 WMW or its progeny, or a plant comprising all but 1, 2, or 3 or more of the morphological and physiological characteristics of NUN 11603 WMW (e.g., as listed in Table 1 and/or 2), with a different watermelon plant, and wherein one or more offspring of the crossing are subject to one or more plant breeding techniques: recurrent selection, backcrossing, pedigree breeding, mass selection, mutation breeding and genetic marker enhanced selection (see, e.g., Vidavsky and Czosnek, (1998) Phytopathology 88(9): 910-4). For breeding methods in general, see, e.g., Principles of Plant Genetics and Breeding, 2007, George Acquaah, Blackwell Publishing, ISBN-13: 978-1-4051-3646-4.

In yet another aspect, the disclosure provides a method of producing a plant, comprising selfing a NUN 11603 WMW plant one or more times, and selecting a progeny plant from said selfing. In one aspect, the progeny plant retains all or all but one, two or three of the physiological and morphological characteristic of NUN 11603 WMW described above when grown under the same environmental conditions. In a different aspect, the progeny plant comprises all of the physiological and morphological characteristic of NUN 11603 WMW of Table 1 and/or Table 2.

In other aspects, the disclosure provides a progeny plant of NUN 11603 WMW such as a progeny plant obtained by further breeding of NUN 11603 WMW. Further breeding with NUN 11603 WMW includes selfing that variety and/or cross-pollinating NUN 11603 WMW with another watermelon plant one or more times. In particular, the disclosure provides for a progeny plant that retains all the morphological and physiological characteristics of NUN 11603 WMW or, in another aspect, a progeny plant that retains all, or all but one, two or three, of the morphological and physiological characteristics of NUN 11603 WMW, optionally all or all but one, two or three of the characteristics as listed in Table 1 and/or 2, determined at the 5% significance level for numerical characteristics, when grown under the same environmental conditions. In an aspect, the progeny is a first generation progeny, i.e., the ovule or the pollen (or both) used in the crossing is an ovule or pollen of NUN 11603 WMW, where the pollen comes from an anther of NUN 11603 WMW and the ovule comes from an ovary of NUN 11603 WMW. In another aspect, the disclosure provides for a vegetative reproduction of NUN 11603 WMW and a plant having all, or all but 1, 2, or 3 of the physiological and morphological characteristics of NUN 11603 WMW (e.g., as listed in Table 1 and/or 2).

The disclosure also provides a method for collecting pollen of NUN 11603 WMW, comprising collecting pollen from a NUN 11603 WMW plant. Alternatively, the method comprises growing a NUN 11603 WMW plant until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a watermelon flower.

In a particular aspect, pollen of NUN 11603 WMW is used to pollinate triploid watermelons, which induces them to set fruit. Thus, NUN 11603 WMW can be used as a pollenizer, optionally by interplanting with triploid watermelons in a field. The disclosure also includes a multitude of NUN 11603 WMW.

The morphological and/or physiological differences between two different individual plants described herein (e.g., between NUN 11603 WMW and a progeny of NUN 11603 WMW) or between a plant of NUN 11603 WMW or progeny of said variety, or a plant having all, or all but 1, 2, or 3, of the physiological and morphological characteristics of NUN 11603 WMW (or all, or all but 1, 2, or 3 of the characteristics as listed in Table 1 and/or 2) and another known variety can easily be established by growing said variety under the same environmental conditions (in the same field, optionally next to each other), preferably repeated in several locations which are suitable for cultivation of NUN 11603 WMW, and measuring the morphological and physiological characteristics of a representative number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, maturity, days from seeding to harvest, plant habit, plant attitude, leaf shape, leaf color, blistering, numbers of flowers per leaf axil, number of calyx lobes, number of petals, fruit group, immature fruit color, mature fruit color, flavor, fruit glossiness, fruit size, fruit shape, average number of fruits per plant, seed size, seed weight, disease resistance, and insect resistance can be measured and directly compared for species of watermelon. Thus, the disclosure comprises watermelon plant having one, two or three physiological and/or morphological characteristics which are different from those of the plant of NUN 11603 WMW and which otherwise has all the physiological and morphological characteristics of the plant of NUN 11603 WMW, when determined at the 5% significance level for plants grown under the same environmental conditions. In another aspect, the different characteristic is affected by a mutation, optionally induced mutation, or by transformation.

The morphological and physiological characteristics of NUN 11603 WMW are provided in the Examples, in Table 1 and/or 2, as collected in a trial according to USDA and/or UPOV standards. The morphological and/or physiological characteristics may vary somewhat with variation in the environment (such as temperature, light intensity, day length, humidity, soil, fertilizer use, disease vectors), which is why a comparison under the same environmental conditions is preferred. Colors can best be measured using the Royal Horticultural Society (RHS) Chart.

Also, at-harvest and/or post-harvest characteristics of fruits can be compared, such as cold storage holding quality, post-harvest flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

The disclosure provides for methods of producing a plant comprising all but 1, 2, or 3 or more of the morphological and physiological characteristics of NUN 11603 WMW (e.g., as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 11603 WMW if its DNA fingerprint is at least 80%, 90%, 95% or 98% identical to the fingerprint of NUN 11603 WMW. In a particular aspect AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Parvathaneni et al., J. Crop Sci. Biotech. 2011 (March) 14 (1): 39-43). The disclosure also provides a plant obtained or selected by applying these methods on NUN 11603 WMW. Such a plant may be produced by traditional breeding techniques, or mutation or transformation or in another aspect, a plant may simply be identified and selected amongst plants of said variety, or progeny of said variety, e.g., by identifying a variant of NUN 11603 WMW which variant differs from the variety described herein watermelon in one, two or three of the morphological and/or physiological characteristics (e.g., characteristics listed in Table 1 and/or 2). In one aspect, the disclosure provides a NUN 11603 WMW plant having a Jaccard's Similarity index with NUN 11603 WMW of at least 0.8, e.g., at least 0.85, 0.9, 0.95, 0.98 or even at least 0.99.

In some aspects, the disclosure provides a watermelon plant comprising genomic DNA having at least 95%, 96%, 97%, 98% or 99% sequence identity compared to the genomic DNA sequence of a plant of NUN 11603 WMW as deposited under Accession Number NCIMB 43061. In some aspects, the watermelon plant further comprises all or all but 1, 2, or 3 of the morphological and physiological characteristics of NUN 11603 WMW (e.g., as listed in Table 1 and/or 2). In other aspects, the watermelon plant is a hybrid derived from a seed or plant of NUN 11603 WMW.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

The disclosure also provides methods for determining the identity of parental lines of plants described herein, in particular the identity of the female line. US2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of NUN 11603 WMW or is a progeny of NUN 11603 WMW, because the seed coat of the seed is a maternal tissue genetically identical to NUN 11603 WMW. In one aspect, the disclosure relates to a maternal tissue of NUN 11603 WMW. In another aspect, the disclosure relates to a watermelon seed comprising a maternal tissue of NUN 11603 WMW. In another particular aspect, the disclosure provides a method of identifying the female parental line of NUN 11603 WMW by analyzing the seed coat of a seed of that variety. In another aspect, the skilled person can determine whether a seed is grown on NUN 11603 WMW by analysing the seed coat or another maternal tissue of said seed.

By crossing and/or selfing (one or more) single traits may be introduced into NUN 11603 WMW (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 11603 WMW by breeding with said variety.

Any pest or disease resistance genes may be introduced into NUN 11603 WMW, progeny of NUN 11603 WMW or into a plant comprising all but 1, 2, or 3 or more of the morphological and physiological characteristics of NUN 11603 WMW (e.g. as listed in Table 1 and/or 2). Resistance to one or more of the following diseases or pests may be introduced into plants described herein: *Colletotrichum orbiculare* (Anthracnose), *Pseudoperonospora cubensis* (Downy Mildew), *Fusarium oxysporum* f. sp. *neveum* (*Fusarium* Wilt), *Didymella bryoniae* (Gummy Stem Blight), *Podosphaera xanthii* (Powdery Mildew), *Verticillium* sp. (*Verticillium* Wilt), Squash Mosaic Virus, Watermelon Mosaic Virus (WMV), Cucumber Mosaic Virus (CMV), *Papaya* Ringspot Virus (PRWV-W), Zucchini Yellow Mosaic Virus (ZYMV), Cucurbit Yellow Stunting Disorder Virus (CYSDV), *Macrophomina phaseolina* (Charcoal Rot), *Monosporascus cannonballus* (*Monosporascus* Vine Decline), Sunburn, Root Knot, and/or *Bemisia tabaci* (Silverleaf Whitefly). Other resistance genes, against pathogenic viruses, fungi, bacteria, nematodes, insects or other pests may also be introduced.

In one aspect, a plant of NUN 11603 WMW may also be mutated (by e.g., irradiation, chemical mutagenesis, heat treatment, etc.) and mutated seeds or plants may be selected in order to change one or more characteristics of said variety. Methods such as TILLING may be applied to populations in order to identify mutants. Similarly, NUN 11603 WMW may be transformed and regenerated, whereby one or more chimeric genes are introduced into the variety or into a plant comprising all but 1, 2, 3, or more of the morphological and physiological characteristics (e.g., as listed in Table 1 and/or 2 and/or 3). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, or tolerance for protection, etc.) can be introduced into NUN 11603 WMW, or progeny of said variety, by transforming said variety or progeny of said variety with a transgene that confers the desired trait, wherein the transformed plant retains all or all but one, two or three of the morphological and/or physiological characteristics of NUN 11603 WMW and contains the desired trait. In another aspect, the transformation or mutation confers a trait wherein the trait is yield, storage properties, color, flavor, male sterility, herbicide tolerance, insect resistance, pest resistance, disease resistance, environmental stress tolerance, modified carbohydrate metabolism, modified protein metabolism or occurs in the intense gene.

The disclosure also provides a plant or a plant cell comprising a desired trait produced by mutating at least one cell of NUN 11603 WMW and selecting a cell or a plant comprising the desired trait, wherein the mutated plant retains all or all but one, two or three of the morphological and physiological characteristics of NUN 11603 WMW, and contains the desired trait and wherein a representative sample of seed of NUN 11603 WMW will be deposited under Accession Number NCIMB 43061. In a further aspect, the transformation or mutation confers a trait wherein the trait is yield, storage properties, color, flavor, male sterility, herbicide tolerance, insect resistance, pest resistance, disease resistance, environmental stress tolerance, modified carbohydrate metabolism, modified protein metabolism or occurs in the intense gene.

In one aspect, the disclosure provides a method for inducing mutation in NUN 11603 WMW comprising:

a. exposing a seed, a plant or a plant part or a cell of NUN 11603 WMW to a mutagenic compound or to radiation, wherein a representative sample of seed of NUN 11603 WMW is deposited under Accession Number NCIMB 43061;
b. selecting a seed, a plant or a plant part or a cell of NUN 11603 WMW having a mutation; and
c. optionally growing and/or multiplying the seed, plant or plant part or cell of NUN 11603 WMW having the mutation.

The disclosure also provides a plant having one, two or three physiological and/or morphological characteristics which are different from those of NUN 11603 WMW and which otherwise has all the physiological and morphological characteristics of said variety, wherein a representative sample of seed of variety NUN 11603 WMW has been deposited under Accession Number NCIMB 43061. In particular, variants which differ from NUN 11603 WMW in no, one, two or three of the characteristics mentioned in Table 1 and/or 2 are encompassed.

A part of NUN 11603 WMW (or of progeny of said variety or of a plant having all physiological and/or morphological characteristics but one, two or three which are different from those of said variety) encompasses any cells, tissues, organs obtainable from the seedlings or plants, such as but not limited to: a watermelon fruit or a part thereof, a cutting, hypocotyl, cotyledon, seed coat, pollen and the like. Such parts can be stored and/or processed further. The disclosure further provides for food or feed products comprising a part of NUN 11603 WMW or a part of progeny of said variety, or a part of a plant having all but one, two or three physiological and/or morphological characteristics of NUN 11603 WMW, comprising one or more of such parts, optionally processed (such as canned, chopped, cooked, roasted, in a sauce, in a sandwich, pasted, pureed or concentrated, juiced, frozen, dried, pickled, or powdered).

The disclosure also provides a plant comprising at least a first set of the chromosomes of NUN 11603 WMW, a sample of seed to be deposited under Accession Number NCIMB 43061, optionally further comprising a single locus conversion. In another aspect, the single locus conversion confers a trait wherein the trait is yield, storage, color, flavor, male sterility, herbicide tolerance, insect resistance, pest resistance, disease resistance, environmental stress tolerance, modified carbohydrate metabolism, modified protein metabolism and ripening.

In one aspect, the disclosure provides a haploid plant and/or a doubled haploid plant of NUN 11603 WMW, or a plant having all but one, two or three physiological and/or morphological characteristics of NUN 11603 WMW, or progeny of any of these. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent and regenerating the cells or tissues into a whole plant.

In yet another aspect, the disclosure provides for haploid plants and/or doubled haploid plants derived from NUN 11603 WMW that, when combined, make a set of parents of NUN 11603 WMW. The haploid plant and/or the doubled haploid plant of NUN 11603 WMW can be used in a method for generating parental lines of NUN 11603 WMW.

In another aspect, the disclosure comprises a method for making doubled haploid cells from haploid cells of NUN 11603 WMW comprises doubling cells of NUN 11603

WMW with a chromosome doubling agent such as colchicine treatment (see, e.g., Nikolova and Niemirowicz-Szczytt (1996) Acta Soc Bot Pol 65:311-317).

Using methods known in the art such as "reverse synthesis of breeding lines" or "reverse breeding", it is possible to produce parental lines for a hybrid plant such as NUN 11603 WMW. A skilled person can take any individual heterozygous plant (called a "phenotypically superior plant" in Example 2 of US2015/0245570 hereby incorporated by reference in its entirety; NUN 11603 WMW is such a plant) and generate a combination of parental lines (reverse breeding parental lines) that, when crossed, produce the NUN 11603 WMW. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., NUN 11603 WMW), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of NUN 11603 WMW, which when crossed reconstitute the genome of NUN 11603 WMW, comprising:
  a. defining a set of genetic markers that are present in a first homozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous forms (B vs. A, or A vs. B); and
  d. optionally repeating steps b) and c) until at least one pair of progeny organisms that have complementary alleles for at least a subset of the genetic markers has been selected as parental lines for a hybrid.

The disclosure relates to a method of producing a combination of parental lines of a plant of NUN 11603 WMW, comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of NUN 11603 WMW when these parental lines are crossed. In still another aspect, the disclosure relates to a combination of parental lines from which a seed or plant having all physiological and/or morphological characteristics of NUN 11603 WMW (when the characteristics are determined at the 5% significance level for plants grown under the same conditions).

In another aspect, the disclosure provides a method of introducing a single locus conversion or single trait conversion or a desired trait into NUN 11603 WMW comprising:
  a. obtaining a combination of a parental lines of NUN 11603 WMW, optionally through reverse synthesis of breeding lines;
  b. introducing a single locus conversion in at least one of the parents of step a; and
  c. crossing the converted parent with the other parent of step a to obtain seed of NUN 11603 WMW.

A combination of a male and a female parental line of NUN 11603 WMW can be generated by methods described herein, for example, through reverse synthesis of breeding lines.

In another aspect, the disclosure provides a method of introducing a single locus conversion or single trait conversion or a desired trait into NUN 11603 WMW, comprising introducing a single locus conversion in at least one of the parents of NUN 11603 WMW; and crossing the converted parent with the other parent of NUN 11603 WMW, to obtain seed of said variety.

In another aspect, introducing a single locus conversion in at least one of the parent plants comprises:
  i. obtaining a cell or tissue culture of cells of the parental line of NUN 11603 WMW;
  ii. genetically transforming or mutating said cells;
  iii. growing the cells into a plant; and
  iv. optionally selecting plants that contain the single locus conversion, the single trait conversion or the desired trait.

In another method, the step of introducing a single locus conversion in at least one of the parents comprises genetically transforming or mutating cells the parental line of NUN 11603 WMW; growing the cells into a plant; and optionally selecting plants that contain the single locus conversion, the single trait conversion or the desired trait.

In another aspect, introducing a single locus conversion in at least one of the parent plants comprises:
  i. crossing the parental line of NUN 11603 WMW with a second watermelon plant comprising the single locus conversion, the single trait conversion or the desired trait;
  ii. selecting F1 progeny plants that contain the single locus conversion, the single trait conversion or the desired trait;
  iii. crossing said selected progeny plants of step ii with the parental line of step i, to produce a backcross progeny plant;
  iv. selecting backcross progeny plants comprising the single locus conversion, the single trait conversion or the desired trait and otherwise all or all but one, two or three of the morphological and physiological characteristics the parental line of step i to produce selected backcross progeny plants; and
  v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions. The disclosure further relates to plants obtained by this method.

In any of the above methods, where the single locus conversion concerns a trait, the trait may be yield or pest resistance or disease resistance. In one aspect, the trait is disease resistance and the resistance is conferred to *Colletotrichum orbiculare* (Anthracnose), *Pseudoperonospora cubensis* (Downy Mildew), *Fusarium oxysporum* f. sp. *neveum* (*Fusarium* Wilt), *Didymella bryoniae* (Gummy Stem Blight), *Podosphaera xanthii* (Powdery Mildew), *Verticillium* sp. (*Verticillium* Wilt), Squash Mosaic Virus, Watermelon Mosaic Virus (WMV), Cucumber Mosaic Virus (CMV), *Papaya* Ringspot Virus (PRWV-W), Zucchini Yellow Mosaic Virus (ZYMV), Cucurbit Yellow Stunting Disorder Virus (CYSDV), *Macrophomina phaseolina* (Charcoal Rot), *Monosporascus cannonballus* (*Monosporascus* Vine Decline), Sunburn, Root Knot, or *Bemisia tabaci* (Silverleaf Whitefly). Other resistance genes, against pathogenic viruses, fungi, bacteria, nematodes, insects or other pests may also be introduced.

The disclosure also provides a combination of parental lines which, when crossed, produce a seed or plant having all physiological and/or morphological characteristics of NUN 11603 WMW but one, two or three which are different (when grown under the same environmental conditions), as well as a seed or plant having all physiological and/or morphological characteristics of NUN 11603 WMW but one, two or three which are different (when the characteristics are determined at the 5% significance level for plants grown under the same conditions).

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

Watermelons may also be grown for use as rootstocks (stocks) or scions. Typically, different types of watermelons are grafted to enhance disease resistance, which is usually conferred by the rootstock, while retaining the horticultural qualities usually conferred by the scion. It is not uncommon for grafting to occur between cultivated watermelon varieties and related watermelon species. Methods of grafting and vegetative propagation are well-known in the art.

In another aspect, the disclosure provides to a plant comprising a rootstock or scion of NUN 11603 WMW.

All documents (e.g., patent publications) are herein incorporated by reference in their entirety, including the following cited references:

UPOV, Guidelines for the Conduct of Tests for Distinctness, Uniformity and Stability, TG142/5, world-wide web at upov.int/edocs/tgdocs/en/tg142.pdf.

US Department of Agriculture, Objective Description of Variety—Watermelon (*Citrullus lanatus*)", world-wide web at ams.usda.gov/under services/plant-variety-protection/pvpo-c-forms under watermelon.

Acquaah, G., "Principles of Plant Genetics and Breeding", Blackwell Publishing, 2007, ISBN-13: 978-1-4051-3646-4

Compton, M., et al., "Use of Tissue Culture and Biotechnology for the Genetic Improvement of Watermelon", Plant Cell, Tissue and Organ Culture, 2004, vol. 77, pp. 231-243

Eigsti, O., "About our Cover", HortScience, 1971, vol. 6, pp. 1-2

Hayata, Y., et. al., "Synthetic Cytokinin-1-(2=chloro=4=pyridyl)-3-phenylurea (CPPU)-Promotes Fruit Set and Induces Parthenocarpy in Watermelon", Society of Horticultural Science, 1995, vol. 120(6), pp. 997-1000

Kihara, H., "Triploid Watermelon", Proceedings of American Society for Horticultural Science, 1951, vol. 58, pp. 217-230

Moussa, H., et. al., "Parthenocarpy of Watermelon Cultivars Induced by γ-Irradiation", Russian Journal of Plant Physiology, 2010, vol. 57, no. 4, pp. 574-581

Parvathaneni, R. K., et al., "Fingerprinting in Cucumber and Melon (*Cucumis* spp.) genotypes Using Morphological and ISSR Markers", Journal of Crop Science and Biotechnology, 2011, vol. 14, no. 1, pp. 39-43. DOI No. 10.1007/s12892-010-0080-1.

Rice, P., et al., "EMBOSS: The European Molecular Biology Open Software Suite", Trends in Genetics, 2000, vol. 16, Issue 6. pp. 276-277.

Vidavsky, F., et. al., "Tomato Breeding Lines Resistant and Tolerant to Tomato Yellow Leaf Curl Virus Issued from *Lycopersicum hirsutum*", The American Phytopathology Society, 1998, vol. 88, no. 9, pp. 910-914.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049

WO2010/111031

US2015/0126380

US2015/0245570

US2006/0168701

EXAMPLES

Development of NUN 11603 WMW

The hybrid NUN 11603 WMW was developed from a male and female proprietary inbred line of Nunhems. The female and male parents were crossed to produce hybrid (F1) seeds of NUN 11603 WMW. The seeds of NUN 11603 WMW can be grown to produce hybrid plants and parts thereof (e.g., watermelon fruit). The hybrid NUN 11603 WMW can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 11603 WMW is uniform and stable.

Deposit Information

A total of 2500 seeds of the hybrid variety NUN 11603 WMW was deposited according to the Budapest Treaty by Nunhems B.V. on May 31, 2018, at the NCIMB Ltd., Ferguson Building, Craibstone Estate, Bucksbun, Aberdeen AB21 9YA, United Kingdom (NCIMB). The deposit will be assigned NCIMB number 43061. A deposit of NUN 11603 WMW and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 U.S.C. § 2321 et seq.).

The most similar variety to NUN 11603 WMW refers to variety NUN 4001 WM, a variety from Nunhems B.V., with the commercial name Premium.

In Table 1 and/or 2, a comparison between NUN 11603 WMW and the Reference variety are shown based on a trial in the USA during the trial season 2018. Trial location: Esparto, Calif.; Transplanting date: Jul. 13, 2018; Harvesting date: Sep. 11, 2018.

One replication of 30 plants per variety, from which at least 15 plants or plant parts were randomly selected and were used to measure characteristics. For numerical characteristics averages were calculated. For non-numerical characteristics, the type/degree were determined. In Table 1 and/or 2, the USDA descriptors of NUN 11603 WMW and the Reference Variety are shown.

In one aspect, the disclosure provides a plant having the physiological and morphological characteristics of NUN 11603 WMW as presented in Tables 1 and/or 2.

TABLE 1

Objective description of NUN 11603 WMW and Reference Variety (USDA Descriptors); significant differences are highlighted in bold, where quantitative values are mentioned these are statistically different between NUN 11603 WMW and the Reference Variety using an ANOVA Tukey test.

| USDA Descriptors | NUN 11603 WMW (Hiromi) | NUN 4001 WM (Premium) |
|---|---|---|
| General Fruit Type | | |
| Fruit type: 1 = Oblong; 2 = Round Large; 3 = Round small (icebox); 4 = Other | 2 | 2 |
| Area of best adaptation | | |
| Region: 1 = Southern US; 2 = Northeast/Central US; 3 = Southwest US; 4 = Most US Areas; 5 = Other | 4 | 4 |
| Maturity | | |
| No. of days from emergence to anthesis | NA | NA |
| No. of days from pollination to maturity | NA | NA |
| Days Relative Maturity (as reported in seed catalogs) | NA | NA |
| Maturity category: 1 = early; 2 = medium; 3 = late | 1 | 1 |
| Ploidy | | |
| 1 = diploid; 2 = tetraploid; 3 = triploid | 2 | 1 |
| Plant | | |
| Cotyledon shape: 1 = flat; 2 = folded | NA | NA |
| Plant sex form: 1 = monoecious; 2 = andromonoecious | 1 | 1 |
| No. of main stems at crown | 5.1 | 6.4 |
| No. of flowers per plant at first fruit set: | | |
| Staminate: | NA | NA |
| Pistilate: | NA | NA |
| Perfect: | NA | NA |
| Stem | | |
| Stem shape (cross section:) 1 = round; 2 = angular | 2 | 2 |
| Diameter at second node (mm) | 5.5 | 6.1 |
| Stem surface: 1 = glabrous; 2 = scabrous; 3 = pubescent; 4 = bristled | 3 | 3 |
| Vine length (cm) (at last harvest) | NA | NA |
| No. of Internodes (at last harvest) | NA | NA |
| Ratio Vine length (cm): No of internodes (at last harvest) | NA | NA |
| Leaf | | |
| Leaf shape: 1 = ovate; 2 = obovate; 3 = round | 1 | 1 |
| Leaf lobes: 1 = none; 2 = lobed | 2 | 2 |
| Leaf length (cm) | 13.4 | 14.5 |
| Leaf width (cm) | 13.2 | 12.7 |
| Leaf size: 1 = longer than wide; 2 = length-width equal; 3 = wider than long | 2 | 1 |
| Dorsal surface pubescence: 1 = smooth; 2 = pubescent | 2 | 2 |
| Ventral surface pubescence: 1 = smooth; 2 = pubescent | 2 | 2 |
| Leaf color: 1 = light green; 2 = gray green; 3 = medium green; 4 = dark green (Color chart value (RHS)) | NA | NA |
| Flower | | |
| Diameter across Staminate (cm) | NA | NA |
| Diameter across Pistillate (cm) | NA | NA |
| Diameter across Perfect (cm) | NA | NA |
| Flower color: 1 = lemon yellow; 2 = yellow; 3 = orange; 4 = other (Color chart value (RHS)) | 2 (RHS2B) | 2 (RHS2B) |
| Mature Fruit | | |
| Fruit shape: 1 = round; 2 = oval; 3 = cylindrical | 1 | 1/2 |
| Long (cm) | 16.8 | 19.2 |
| Diameter at midsection (cm) | 14.9 | 16.2 |
| Average weight (kg) | 1.9 | 2.7 |
| Maximum fruit weight (kg) | 3.2 | 3.0 |
| Index = length ÷ diameter × 10 | 11.3 | 11.9 |
| Fruit surface: 1 = smooth; 2 = slightly grooved; 3 = deeply grooved | 2 | 2 |
| Skin color pattern: 1 = solid (one color); 2 = stripe; 3 = mottle/net | 2 | 2 |
| Primary color: 1 = Yellow Green (Desert King); 2 = Light Green (Charleston Gray); 3 = Medium Green (Sugar baby); 4 = dark green (Florida Giant); 5 = Other (Color chart value (RHS)) | 2 (139A) | 2 (139A) |
| Secondary color: | 2 (RHS | 1 (RHS |

TABLE 1-continued

Objective description of NUN 11603 WMW and Reference Variety (USDA Descriptors); significant differences are highlighted in bold, where quantitative values are mentioned these are statistically different between NUN 11603 WMW and the Reference Variety using an ANOVA Tukey test.

| USDA Descriptors | NUN 11603 WMW (Hiromi) | NUN 4001 WM (Premium) |
|---|---|---|
| 1 = Yellow Green; 2 = Light Green; 3 = Medium green; 4 = dark green; 5 = Other (Color chart value (RHS)) | 139D) | 138C) |
| Rind | | |
| Rind texture: 1 = tender; 2 = brittle; 3 = tough | 3 | 3 |
| Thickness blossom end (mm) | 4.2 | 4.8 |
| Thickness sides (mm) | 8.5 | 9.1 |
| Flesh | | |
| Flesh texture: 1 = crisp; 2 = soft | 1 | 1 |
| Flesh coarseness: 1 = course fibrous; 2 = fine-little fiber | 2 | 2 |
| Flesh color: 1 = white; 2 = yellow; 3 = orange; 4 = pink; 5 = red; 6 = dark red (Color chart value (RHS)) | 5 (39A) | 5 (39A) |
| Refractometer: % Soluble solids of juice (Center of fruit) | 11.5 | 12.3 |

TABLE 2

Objective description of NUN 11603 WMW and the Reference Variety (Non-USDA Descriptors); significant differences are highlighted in bold, where quantitative values are mentioned these are statistically significant different between NUN 11603 WMW and the Reference Variety using the ANOVA Tukey test.

| Non-USDA Descriptors | NUN 11603 WMW (Hiromi) | NUN 4001 WM (Premium) |
|---|---|---|
| Petiole diameter of leaf (mm) | 4.6 | 4.8 |
| Petiole length of leaf (cm) | 10.6 | 12.0 |
| Petiole diameter of mature fruit (mm) | 4.6 | 4.8 |
| Stem end thickness (mm) | 7.6 | 11.2 |
| Fruit firmness (kg) | 1.8 | 1.2 |

Tables 1 and 2 contain typical values. Values may vary due to environment. Other values that are substantially equivalent are also within the scope of the invention. N.A.=not applicable; n.r.=not recorded.

The invention claimed is:

1. A plant, plant part, or seed of watermelon variety NUN 11603 WMW, wherein a representative sample of seed of said watermelon variety NUN 11603 WMW is deposited under Accession Number NCIMB 43061.

2. The plant part of claim 1, wherein said plant part is a leaf, pollen, an ovule, a fruit, a scion, a root, a rootstock, a cutting, a flower, or a cell.

3. A seed that produces the plant of claim 1.

4. A watermelon plant, or a part thereof having all the physiological and morphological characteristics of the plant of claim 1.

5. A tissue or cell culture comprising cells of the plant of claim 1.

6. The tissue or cell culture according to claim 5, comprising cells or protoplasts from a plant part, wherein the plant part is an embryo, a meristem, a cotyledon, a hypocotyl, pollen, a leaf, an anther, a root, a root tip, a pistil, a petiole, a flower, a fruit, a seed or a stem.

7. A watermelon plant regenerated from the tissue or cell culture of watermelon variety NUN 11603 WMW, wherein the plant has all of the physiological and morphological characteristics of the plant of variety NUN 11603 WMW, and wherein a representative sample of seed of watermelon variety NUN 11603 WMW is deposited under Accession Number NCIMB 43061.

8. A method of producing the plant of claim 1, said method comprising vegetative propagation of watermelon variety NUN 11603 WMW, wherein a representative sample of seed of said watermelon variety NUN 11603 WMW is deposited under Accession Number NCIMB 43061.

9. The method of claim 8, wherein the vegetative propagation comprises regenerating a whole plant from a part of the plant of variety NUN 11603 WMW, wherein a representative sample of seed of said watermelon variety NUN 11603 WMW is deposited under Accession Number NCIMB 43061.

10. The method of claim 9, wherein said part is a cutting, a cell culture or a tissue culture.

11. A vegetative propagated plant of watermelon variety NUN 11603 WMW, or a part thereof, wherein the vegetative propagated plant has all of the physiological and morphological characteristics of the plant of variety NUN 11603 WMW, and wherein a representative sample of seed of watermelon variety NUN 11603 WMW is deposited under Accession Number NCIMB 43061.

12. A method of producing a watermelon plant, comprising crossing the plant of claim 1 with a second watermelon plant at least once, and selecting progeny from said crossing and optionally allowing the progeny to form seed.

13. A watermelon plant having all the physiological and morphological characteristics of the plant of claim 1, wherein a representative sample of seed of watermelon variety NUN 11603 WMW is deposited under Accession Number NCIMB 43061, further comprising a transgene.

14. A plant comprising the scion or rootstock of claim 2.

15. A container comprising the plant, the plant part or the seed of claim 1.

16. A food, feed product or a processed product comprising the plant part of claim 2.

17. A plant of watermelon variety NUN 11603 WMW, further comprising a single locus conversion, wherein said plant has all of the physiological and morphological characteristics of the plant of variety NUN 11603 WMW, wherein a representative sample of seed of watermelon variety NUN 11603 WMW is deposited under Accession Number NCIMB 43061, and wherein the single locus conversion confers male sterility, herbicide tolerance, insect resistance, pest resistance, disease resistance, environmental stress resistance, modified carbohydrate metabolism, modified protein metabolism or ripening.

18. A method of producing a plant having a desired trait, wherein the method comprises mutating a plant of variety NUN 11603 WMW and selecting a plant with a desired trait, wherein the mutated plant contains the desired trait and otherwise retains all of the physiological and morphological characteristics of variety NUN 11603 WMW, wherein a representative sample of seed of watermelon variety NUN 11603 WMW is deposited under Accession Number NCIMB 43061, and wherein the desired trait is male sterility, herbicide tolerance, insect resistance, pest resistance, disease resistance, environmental stress resistance, modified carbohydrate metabolism, modified protein metabolism or ripening.

19. A method of producing a watermelon fruit, comprising growing the plant of claim 1 until it sets fruit and collecting the fruit.

20. A method for inducing a mutation in the plant of claim 1, comprising:
 a. exposing the seed, plant, or plant part of the plant of variety NUN 11603 WNW to a mutagenic chemical or to radiation, wherein a representative sample of seed of said watermelon variety is deposited under Accession Number NCIMB 43061; and
 b. selecting the seed, plant, plant part, or cell of watermelon variety NUN 11603 WMW having a mutation.

\* \* \* \* \*